US00PP18953P2

(12) United States Plant Patent
Heffron

(10) Patent No.: US PP18,953 P2
(45) Date of Patent: Jun. 17, 2008

(54) **NEW GUINEA *IMPATIENS* PLANT NAMED 'BALCELIMPIK'**

(50) Latin Name: *Impatiens hawkeri*
Varietal Denomination: Balcelimpik

(75) Inventor: Leslie Heffron, Hickory, NC (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/605,156

(22) Filed: Nov. 28, 2006

(51) Int. Cl.
*A01H 5/00* (2006.01)

(52) U.S. Cl. ..... Plt./318

(58) Field of Classification Search ..... Plt./318
See application file for complete search history.

(56) References Cited

PUBLICATIONS

Canada Plant Breeders' Rights application No. 06–5302 filed Mar. 9, 2006.
European Plant Breeders' Rights application No. 2006/2338 filed Nov. 16, 2006.

*Primary Examiner*—Anne Marie Grunberg
*Assistant Examiner*—Louanne Krawczewicz Myers
(74) *Attorney, Agent, or Firm*—Audrey Charles

(57) ABSTRACT

A new and distinct cultivar of New Guinea *Impatiens* plant named 'Balcelimpik', characterized by its medium pink-colored flowers, dark green-colored foliage, and vigorous, upright-mounded growth habit.

1 Drawing Sheet

Latin name of genus and species of plant claimed: *Impatiens hawkeri.*
Variety denomination: 'Balcelimpik'.

BACKGROUND OF THE INVENTION

The present invention relates to a new and distinct cultivar of New Guinea *Impatiens* plant botanically known as *Impatiens hawkeri* and hereinafter referred to by the cultivar name 'Balcelimpik'.

The new cultivar originated in a controlled breeding program in Arroyo Grande, Calif. during February 2004. The objective of the breeding program was the development of *Impatiens* cultivars with numerous large flowers, attractive flower coloration, and a freely basal branching growth habit.

The new *Impatiens* cultivar is the result of cross-pollination. The female (seed) parent of the new cultivar is Celebration Pink 'Balcelpink', U.S. Plant Pat. No. 14,645, characterized by its medium pink-colored flowers, medium green-colored foliage, and upright-mounded growth habit. The male (pollen) parent of the new cultivar is the proprietary *Impatiens hawkeri* breeding selection designated 8225-B, not patented, characterized by its medium coral-colored flowers, medium green-colored foliage, and upright growth habit. The new cultivar was discovered and selected as a single flowering plant within the progeny of the above stated cross-pollination during July 2004 in a controlled environment at Arroyo Grande, Calif.

Asexual reproduction of the new cultivar by terminal stem cuttings since July 2004 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balcelimpik' as a new and distinct cultivar of New Guinea *Impatiens* plant:

1. Medium pink-colored flowers;
2. Dark green-colored foliage; and
3. Vigorous, upright-mounded growth habit.

Plants of the new cultivar differ from plants of the male parent primarily in flower color, foliage color, and growth habit.

Of the many commercially available New Guinea *Impatiens* cultivars known to the inventor, the most similar in comparison to the new cultivar is the female parent Celebration Pink 'Balcelpink', U.S. Plant Pat. No. 14,645. However, in side by side comparisons, plants of the new cultivar differ from plants of 'Balcelpink' in the following characteristics:

1. Plants of the new cultivar have larger flowers than plants of 'Balcelpink';
2. Plants of the new cultivar are taller than plants of 'Balcelpink'; and
3. Plants of the new cultivar are narrower than plants of 'Balcelpink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelimpik'. The plants were grown in 4.5 inch pots for 18 weeks in a greenhouse at West Chicago, Ill.

DETAILED BOTANICAL DESCRIPTION

Figure 1:
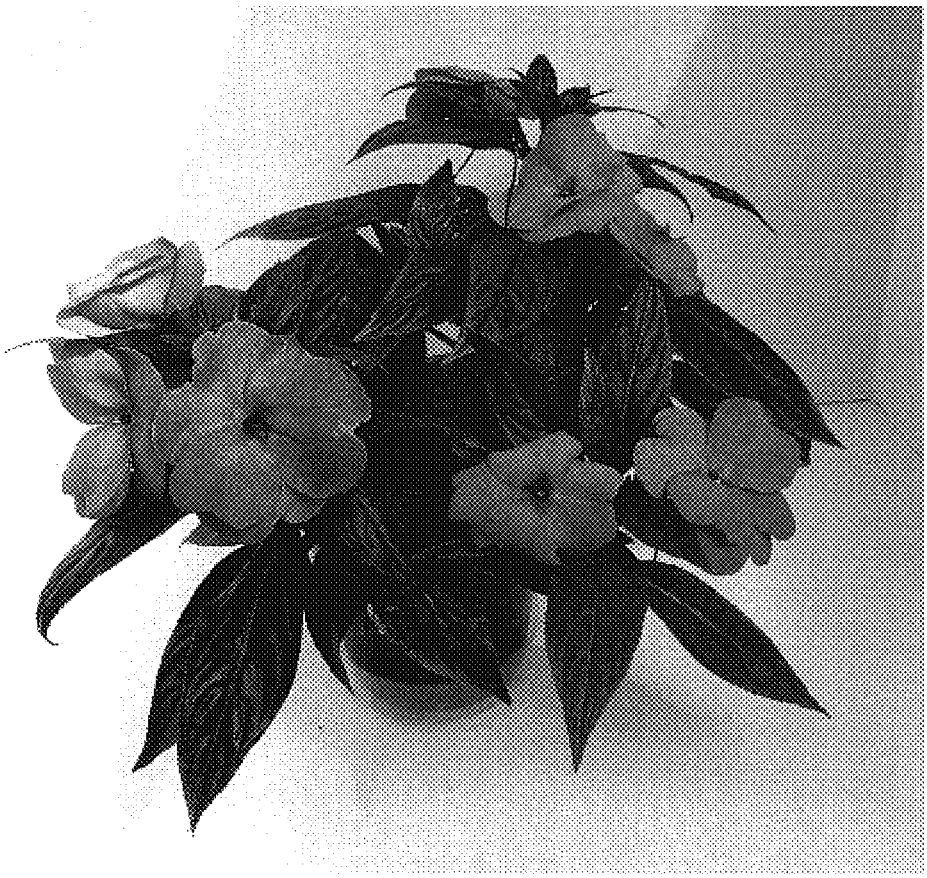
FIG. 1 illustrates a side view of the overall growth and flowering habit of 'Balcelimpik'.
Figure 2:
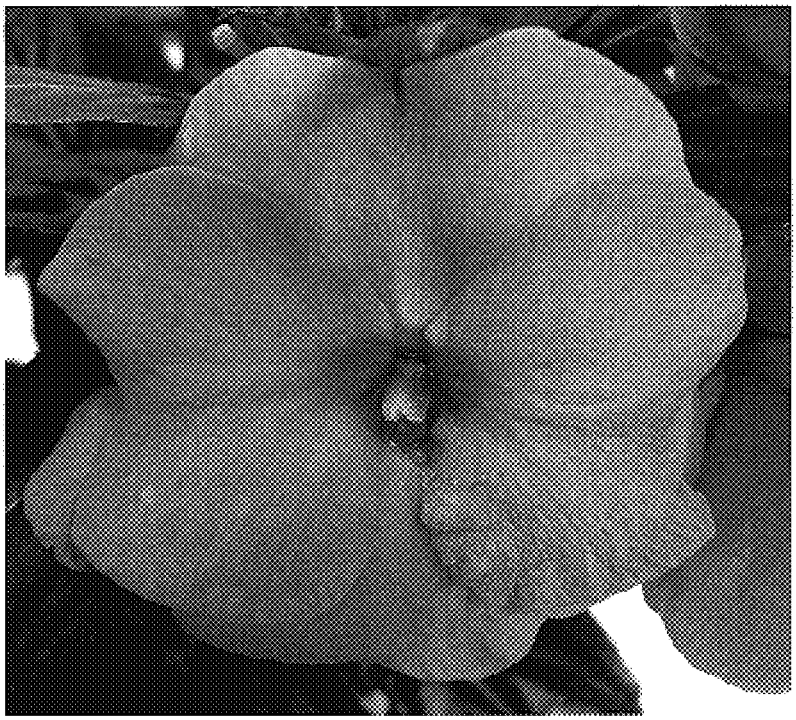
FIG. 2 illustrates a close-up view of an individual flower of 'Balcelimpik'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 7, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 18 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Impatiens hawkeri* cultivar Balcelimpik.

Parentage:

*Female parent.*—Celebration 'Balcelpink', U.S. Plant Pat. No. 14,645.

*Male parent.*—Proprietary *Impatiens hawkeri* breeding selection designated 8225-B, not patented.

Propagation:

*Type cutting.*—Terminal stem.

*Time to initiate roots.*—Approximately 7 to 8 days.

*Time to produce a rooted cutting.*—Approximately 21 to 24 days.

*Root description.*—Fibrous.

*Rooting habit.*—Freely branching.

Plant description:

*Commercial crop time.*—Approximately 7 to 9 weeks from a rooted cutting.

*Growth habit and general appearance.*—Vigorous, upright-mounded.

*Size.*—Height from soil level to top of plant plane: Approximately 18.4 cm. Width: Approximately 38.2 cm.

*Branching habit.*—Freely basal branching. Quantity of main lateral branches per plant: Approximately 5.

*Branch.*—Strength: Strong. Length: Approximately 15.6 cm. Diameter: Approximately 7.0 mm. Length of central internode: Approximately 3.4 cm. Texture: Glabrous. Color of young and mature stems: 144B with overlay of 185A.

Foliage description:

*General description.*—Quantity of leaves per main branch: Approximately 13. Fragrance: None. Form: Simple. Arrangement: In whorls of 3 to 5 leaves.

*Leaves.*—Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of mature leaf at center of stem: Approximately 10.6 cm. Width of mature leaf at center of stem: Approximately 3.6 cm. Texture of upper and lower surfaces: Glabrous. Color of upper surface of young foliage: 147A with venation of 191A and an overlay on midvein of 185B that fades towards leaf apex. Color of lower surface of young foliage: 191B with venation of 191A. Color of upper surface of mature foliage: Darker than 147A with venation of 191A and an overlay on midvein of 185B that fades towards leaf apex. Color of lower surface of mature foliage: 191B with venation of 191A and an overlay on midvein of 185B that fades towards leaf apex.

*Petiole.*—Length: Approximately 1.3 cm. Diameter: Approximately 3.2 mm. Texture: Glabrous. Color: 191C with an overlay of 185B.

Flowering description:

*Flowering habit.*—'Balcelimpik' is freely flowering under outdoor growing conditions with substantially continuous blooming from spring through autumn and year-round in greenhouse environment.

*Lastingness of individual flower on the plant.*—Approximately 5 to 7 days.

Flower description:

*General description.*—Type: Single. Quantity per plant: Approximately 5. Fragrance: None.

*Bud.*—Rate of opening: Generally takes 3 to 4 days for bud to progress from first color to fully open flower. Quantity showing color per plant: Approximately 3.

*Bud just before opening.*—Shape: Ovoid. Length: Approximately 2.0 cm. Diameter: Approximately 1.5 cm. Color: N74B.

*Corolla.*—Shape: Round, cupped when first open with petals turning downward with age. Width: Approximately 7.1 cm. Depth: Approximately 1.9 cm. Borne: Above and below foliage.

*Petals.*—Quantity: 5. Shape (all petals): Obovate. Aspect: Flat. Appearance: Iridescent. Margin: Entire. Apex: Emarginate. Base of upper petal: Truncate. Base of lateral and lower petals: Attenuate. Length of upper petal: Approximately 3.1 cm. Width of upper petal: Approximately 5.3 cm. Length of lateral petals: Approximately 3.2 cm. Width of lateral petals: Approximately 4.2 cm. Length of lower petals: Approximately 3.5 cm. Width of lower petals: Approximately 4.9 cm. Texture of upper and lower surfaces: Glabrous. Color of upper surface when first open: N74B with a central eye of N74A. Color of lower surface when first open: N74C. Color of upper surface when fully open: Between N74C and N74B with a central eye of N74A. Color of lower surface when fully open: Between N74D and N74C.

*Spur.*—Quantity: 1 per flower. Length: Approximately 5.4 cm. Diameter at tip: Approximately 1.0 mm. Diameter at base: Approximately 2.9 mm. Texture: Glabrous. Color: 187C darkening to 187B toward tip with tip of 144C having an overlay of 187C.

*Peduncle.*—Strength: Strong. Aspect: Acute angle to stem. Length: Approximately 4.6 cm. Diameter: Approximately 2.0 mm. Texture: Glabrous. Color: 144B with an overlay of 185A.

*Sepals.*—Quantity per flower: 4, with one fused to base of upper petal. Sepal arrangement: 1 spurred lower sepal located between 2 side (lateral) sepals. Shape of lateral and lower sepals: Ovate. Apex of all sepals:

Acuminate. Margin of all sepals: Entire. Base of lateral sepals: Broadly attenuate. Base of lower sepal modified into a spur. Length of lateral sepals: Approximately 1.5 cm. Width of lateral sepals: Approximately 5.1 mm. Length of lower sepal: Approximately 1.9 cm. Width of lower sepal: Approximately 1.2 cm. Texture of upper and lower surfaces of all sepals: Glabrous. Color of upper and lower surfaces of lateral sepals: 144B with an overlay of 185A and tip of 144B. Color of upper and lower surfaces of lower sepal: Closest to N155B with an overlay of 185D and tip of 144B.

*Reproductive organs.*—Androecium: Stamen quantity: 5 per flower, fused around pistil at apex. Anther shape: Hooded. Anther length: Approximately 2.0 mm. Anther color: N79C. Pollen amount: Abundant. Pollen color: 155D. Gynoecium: Pistil quantity: 1 per flower. Pistil length: Approximately 5.0 mm. Stigma shape: 5-pointed star. Stigma color: Colorless, transparent. Style color: 144A. Ovary texture: Glabrous. Ovary color: 144A.

Seed and fruit production: Neither seed nor fruit production has been observed.

Disease and pest resistance: Resistance to pathogens and pests common to New Guinea *Impatiens* has not been observed.

What is claimed is:

1. A new and distinct cultivar of New Guinea *Impatiens* plant named 'Balcelimpik', substantially as herein shown and described.

* * * * *